US00PP30535P2

(12) United States Plant Patent
Meilland

(10) Patent No.: US PP30,535 P2
(45) Date of Patent: May 28, 2019

(54) BEDDING ROSE PLANT NAMED 'MEIKRONDER'

(50) Latin Name: *Rosa hybrida*
Varietal Denomination: MEIKRONDER

(71) Applicant: The Conard-Pyle Company, West Grove, PA (US)

(72) Inventor: Alain Antoine Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 15/932,682

(22) Filed: Apr. 9, 2018

(51) Int. Cl.
*A01H 5/02* (2018.01)

(52) U.S. Cl.
USPC ..... Plt./101

(58) Field of Classification Search
USPC ..... Plt./101, 130
See application file for complete search history.

(56) References Cited

U.S. PATENT DOCUMENTS

PP11,836 P2 4/2001 Radler

*Primary Examiner* — Annette H Para
(74) *Attorney, Agent, or Firm* — Buchanan Ingersoll & Rooney PC

(57) ABSTRACT

A new and distinct variety of Bedding Rose plant, herein referred to by its cultivar name, 'MEIKRONDER', is provided which forms very abundantly on a nearly continuous basis attractive, cup-shaped, red purple colored blossoms. Attractive, semi-glossy, very dense foliage is formed, which contrasts beautifully with the blossoms. The disease tolerance is very good, particularly against Black Spot. The new variety is well suited for proving attractive ornamentation in the landscape and is very floriferous.

1 Drawing Sheet

Botanical/commercial classification:
Latin name—*Rosa hybrida.*
Common name—Bedding Rose Plant.
Varietal denomination: 'MEIKRONDER'.

SUMMARY OF THE INVENTION

The new variety of *Rosa hybrida* Bedding Rose plant was created by artificial pollination wherein two parents were crossed which previously had been studied in the hope that they would contribute the desired characteristics. The female parent (i.e., the seed parent) was the 'NOAWEL' variety (non-patented in the United States). The male parent (i.e., the pollen parent) was the 'RADRAZZ' variety (U.S. Plant Pat. No. 11,836).

The parentage of the new variety can be summarized as follows:

'NOAWEL' x 'RADRAZZ'

The seeds resulting from the above pollination were sown and small plants were obtained which were physically and biologically different from each other. Selective study resulted in the identification of a single plant of the new variety.

It was found that the new variety of Bedding Rose plant of the present invention possesses the following combination of characteristics:

(a) very abundantly and nearly continuously forms attractive, cup-shaped, red purple colored blossoms,
(b) forms attractive, very dense, semi-glossy foliage,
(c) exhibits very good tolerance to diseases, particularly against Black Spot,
(d) is very floriferous, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'NOAWEL' variety (i.e., the seed parent) exhibits a plant height of near 60 cm on average, whereas the new variety exhibits a plant height of commonly near 75 to 90 cm on average. The 'RADRAZZ' variety (i.e., the pollen parent) displays single form flowers possessing approximately 10 petals on average, while the new variety displays flowers possessing approximately 29-34 petals on average.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEIKRONDER'.

BRIEF DESCRIPTION OF THE PHOTOGRAPH

FIG. 1—illustrates as nearly true as it is reasonably possible to make the same, in a color illustration of this character, typical specimens of the plant parts of the new variety. The rose plants of the new variety were approximately two years of age and were observed during November while budded on their own roots and growing outdoors at Le Cannet des Maures, Var, France. Standard color information and dimensions in centimeters are included at the bottom of the photograph.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of a fully open flower—plan view—obverse.

Element 7—illustrates a specimen of a fully open flower—plan view—reverse.

Element 8—illustrates a specimen of a flower in the course of opening—plan view—obverse.

Element 9—illustrates a specimen of a flower in the course of opening—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 7 leaflets—plan view—under surface.

DETAILED BOTANICAL DESCRIPTION

The chart used in the identification of the colors is that of The Royal Horticultural Society (R.H.S. Colour Chart), London, England. The terminology which precedes reference to the chart has been added to indicate the corresponding color in more common terms. The description is based on the observation of two-year-old specimens of the new variety during November while budded on their own roots and growing outdoors at Le Cannet des Maures, Var, France.

Class: Bedding Rose Plant.

Plant:

*Habit*.—Bushy.

*Height*.—Commonly near 75 to 90 cm on average.

Branches:

*Color*.—Young stems: commonly near Yellow-Green Group 146D. Adult wood: commonly near Yellow-Green Group 146B.

*Thorns*.—Configuration on adult stems: curved downward on the upper surface and concave on the under surface. Long prickles (≥0.5 cm) — quantity: commonly approximately 3 thorns per 10 cm long young stem and commonly 4 thorns per 10 cm long adult stem. Long prickles (≥0.5 cm) — base shape: oval. Long prickles (≥0.5 cm) — size: commonly near 0.5 cm in length on average on young stems and commonly near 0.7 cm in length on average on adult stems. Long prickles (≥0.5 cm) — color: commonly near Greyed-Orange Group 173C on young stems and commonly near Greyed-Orange Group 175A on adult stems. Small prickles (<0.5 cm) — quantity: commonly approximately 23 thorns per 10 cm long young stem and commonly 13 thorns per 10 cm long adult stem. Small prickles (<0.5 cm) — base shape: oval. Small prickles (<0.5 cm) — size: commonly near 0.2 cm in length on average. Small prickles (<0.5 cm) — color: commonly near Greyed-Orange Group 173D on young stems and commonly near Greyed-Orange Group 175A on adult stems.

Foliage:

*General appearance*.—Very dense with a semi-glossy aspect.

*Number of leaflets*.—3, 5, and 7; most often 5 or 7.

*Terminal leaflet*.—Length: approximately 5.5 cm on average. Width: approximately 3.1 cm on average.

*New foliage*.—Upper surface color: commonly near Green Group 137B. Under surface color: commonly near Yellow-Green Group 146C.

*Adult foliage*.—Upper surface color: commonly near Green Group 137A. Under surface color: commonly near Yellow-Green Group 146B.

Leaflets:

*Shape*.—Tip: acuminate. Base: obtuse.

*Texture*.—Leathery.

*General appearance*.—Elliptical.

*Edge*.—Slightly denticulate.

*Serration*.—Small and single.

*Petiole rachis*.—Color of upper surface: commonly near Yellow-Green Group 146C. Color of under surface: commonly near Yellow-Green Group 146C.

*Petioles*.—Upper surface: no glandular. Under surface: few prickles. Color of upper surface: commonly near Yellow-Green Group 146B. Color of under surface: commonly near Yellow-Green Group 146D. Petiole length of terminal leaflet: commonly near 2.5 cm on average.

*Stipules*.—General appearance: adnate, pectinate and narrow. Length: approximately 1.0 cm on average. Width: approximately 0.4 cm on average. Color of upper surface: commonly near Yellow-Green Group 146D. Color of under surface: commonly near Yellow-Green Group 146C.

Inflorescence:

*Number of flowers per stem*.—Generally between 1 and 7 flowers per stem.

*Bud*.—Shape: conical. Size: medium. Length: approximately 2.5 cm on average. Width: approximately 2.0 cm on average. Color as calyx breaks: Upper surface: commonly near Red-Purple Group 66B. Under surface: commonly near Red-Purple Group 66C.

*Sepals*.—Length: approximately 1.2 cm on average. Width: approximately near 0.7 cm on average. Shape: some extensions (approximately 1.0 cm on average). At the top: narrow and longish. At the base: upright. Upper surface: Texture: tomentous. Color: commonly near Yellow-Green Group 146B. Under surface: Texture: smooth. Color: commonly near Yellow-Green Group 146D.

*Receptacle*.—Color: commonly near Yellow-Green Group 146B. Length: approximately 0.7 cm on average. Width: approximately 0.5 cm on average. Surface: smooth. Shape: pitcher shaped.

*Peduncle*.—Length: approximately near 4.6 cm on average. Width: approximately 0.2 cm on average. Surface: smooth. Color: commonly near Yellow-Green Group 146B.

*Flower*.—Average diameter when fully open: approximately 5 to 7 cm on average. Borne: commonly between 1 to 7 flowers per stem. Shape: cup shaped.

Number of petals under normal conditions: approximately 29 to 34 petals on average. Shape of the petal: Base: obtuse. Top: rounded. Texture of the petal: leathery. Petal length: approximately 3.5 cm on average. Petal width: approximately 4.0 cm on average. Petal arrangement: imbricated without petaloids. Petal drop: petals drop off cleanly before drying. Fragrance: none. Color when opening: Upper surface: commonly near Red-Purple Group 66B; little spot at the base is commonly near Yellow Group 2D. Under surface: commonly near Red-Purple Group 66C; little spot at the base is commonly near Yellow Group 2D. Color of the open flower: Upper surface: commonly near Red-Purple Group 66C amply suffused with near Red-Purple Group 66B/A; little spot at the base is commonly near Yellow Group 2D. Under surface: commonly near Red-Purple Group 66C amply suffused with near Red-Purple Group 67C; little spot at the base is near Yellow Group 2D. Anthers: number is approximately 67 on average, length is approximately 0.1 cm on average, coloration is commonly near Yellow-Orange Group 22D, and arrangement is regular around styles. Filaments: length is approximately 0.2 cm on average and coloration is commonly near Yellow Group 2D. Styles: length is approximately 0.2 cm on average, the coloration is commonly near Greyed-Red Group 178A, and the number is approximately 48 on average. Stigmas: size is approximately 0.1 cm on average and the coloration is commonly near Greyed-Red Group 178A. Pollen: not available at this stage. Hips: not available at this stage.

Development:

*Vegetation*.—Very strong.

*Blooming*.—Medium in the season, very abundant and nearly continuous.

*Tolerance to disease*.—Very good, and particularly against Black Spot.

The new 'MEIKRONDER' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Bedding Rose plant characterized by the following combination of characteristics:

(a) very abundantly and nearly continuously forms attractive, cup-shaped, red purple colored blossoms, (b) forms attractive, very dense, semi-glossy foliage, (c) exhibits very good tolerance to diseases, particularly against Black Spot, (d) is very floriferous, and (e) is well suited for providing attractive ornamentation; substantially as herein shown and described.

* * * * *

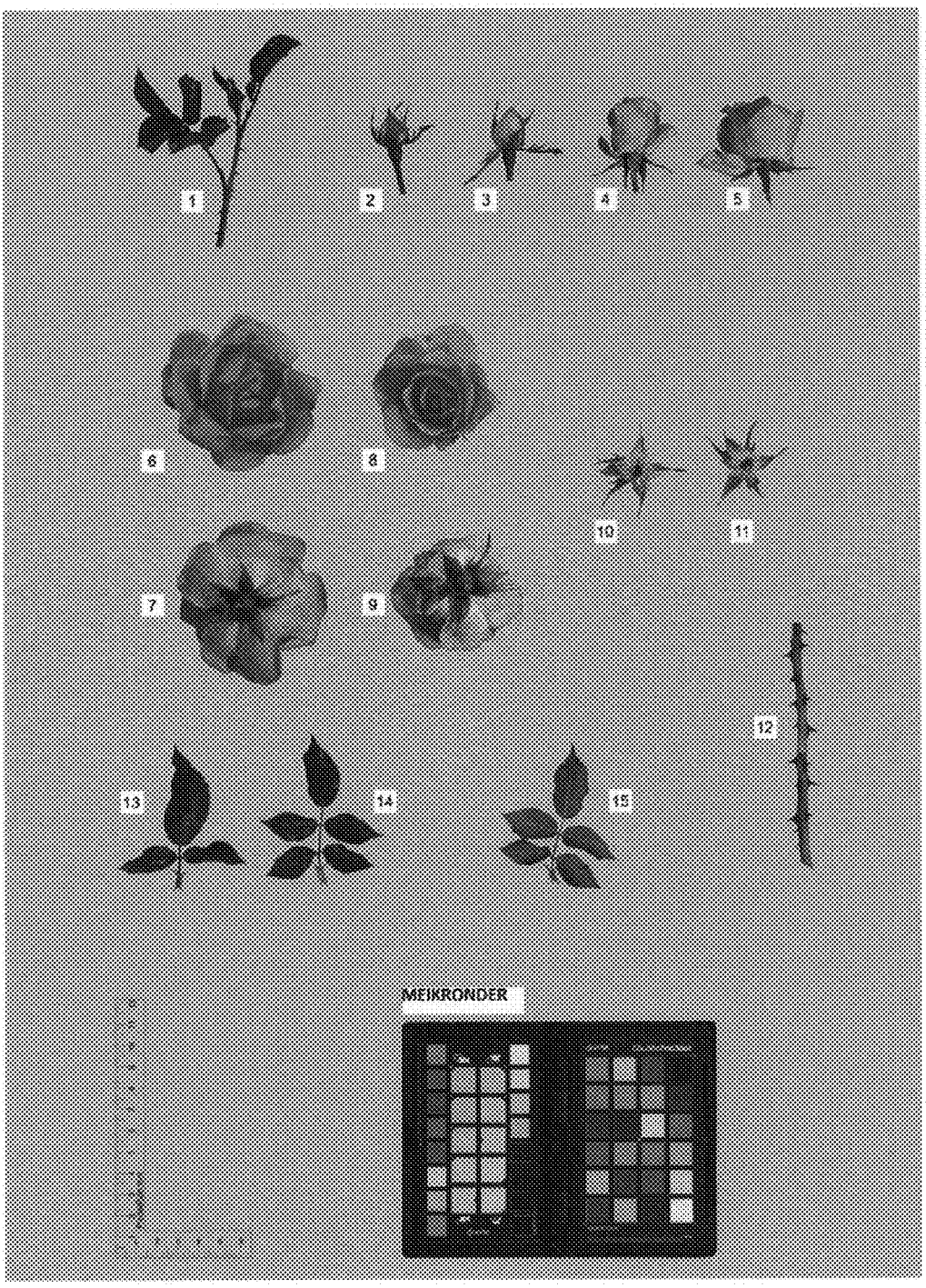
1
2
3
4
5
6
8
10
11
7
9
12
13
14
15
MEIKRONDER